United States Patent
Yoshida

(10) Patent No.: US 6,302,110 B1
(45) Date of Patent: Oct. 16, 2001

(54) DENTAL PROTECTOR AGAINST BRUXISM

(76) Inventor: Nobutaka Yoshida, 9-18, Nipponbashi 2-chome, Chuo-ku, Osaka-shi, Osaka 542-0073 (JP)

( * ) Notice: Subject to any disclaimer, the term of this patent is extended or adjusted under 35 U.S.C. 154(b) by 0 days.

(21) Appl. No.: 09/308,877

(22) PCT Filed: Feb. 18, 1999

(86) PCT No.: PCT/JP99/00145

§ 371 Date: May 25, 1999

§ 102(e) Date: May 25, 1999

(87) PCT Pub. No.: WO99/35997

PCT Pub. Date: Jul. 22, 1999

(30) Foreign Application Priority Data

Jan. 20, 1998 (JP) .................................................. 10-024003

(51) Int. Cl.[7] .................................................... A61F 5/56
(52) U.S. Cl. ......................... 128/848; 128/859; 128/861; 128/862; 602/902
(58) Field of Search ................................... 128/846, 848, 128/859–862; 602/902

(56) References Cited

U.S. PATENT DOCUMENTS

| 5,103,838 | * | 4/1992 | Yousif | 128/859 |
| 5,406,962 | * | 4/1995 | Adell | 128/859 |
| 5,511,562 | * | 4/1996 | Hancock | 128/859 |
| 5,826,581 | * | 10/1998 | Yoshida | 128/862 |

* cited by examiner

*Primary Examiner*—Michael A. Brown
(74) *Attorney, Agent, or Firm*—Vedder Price Kaufman & Kammholz

(57) ABSTRACT

The invention has for its object to provide a dental protector against bruxism adapted to protect the teeth from clenching, insure stability during wear, and applicable to many persons. The dental protector comprises a protective part (2) configured generally in the form of the letter U in conformity with the dental arc and adapted to cover the occlusal faces of the teeth and an engaging part (3) contiguous to the inner circumference of the protective part and adapted to cover the posterior surfaces of the teeth, the lower stratum (2y) of the protective part, which is to contact with the teeth, and the engaging part being formed from a thermoplastic resin having a softening temperature lower than the boiling temperature of water and the upper stratum (2x) of the protective part which is flat being formed from a material which does not soften at the above softening temperature.

11 Claims, 2 Drawing Sheets

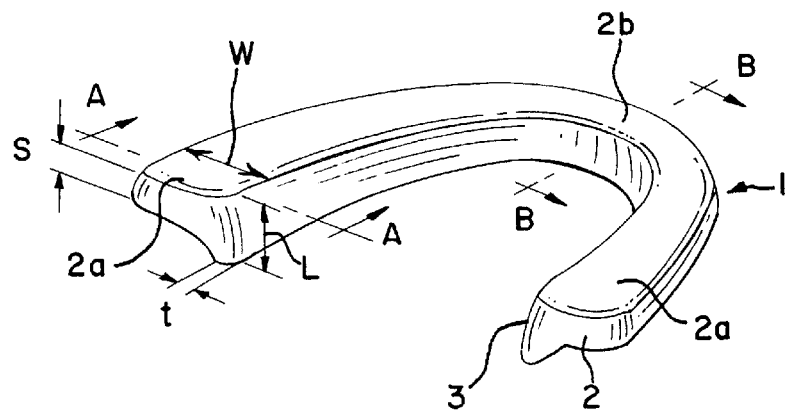
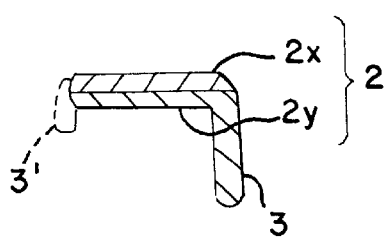 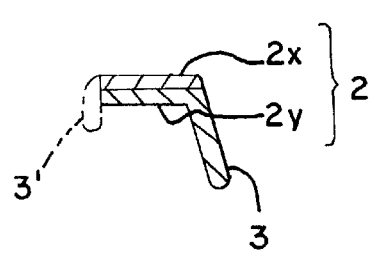
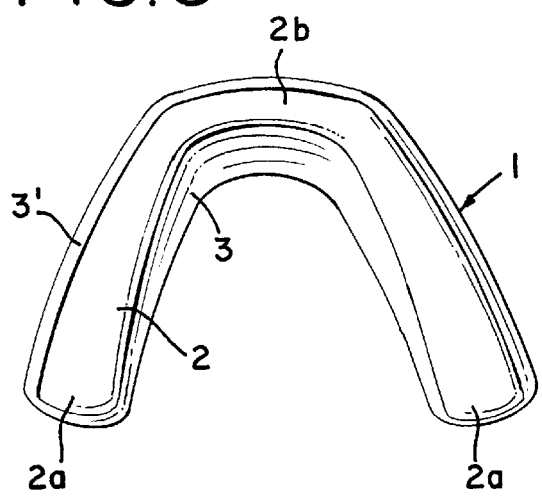 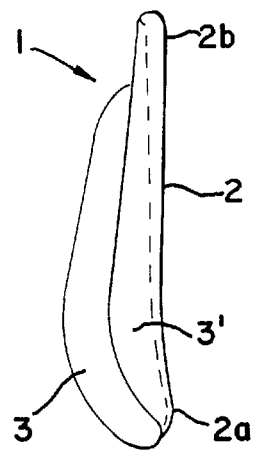

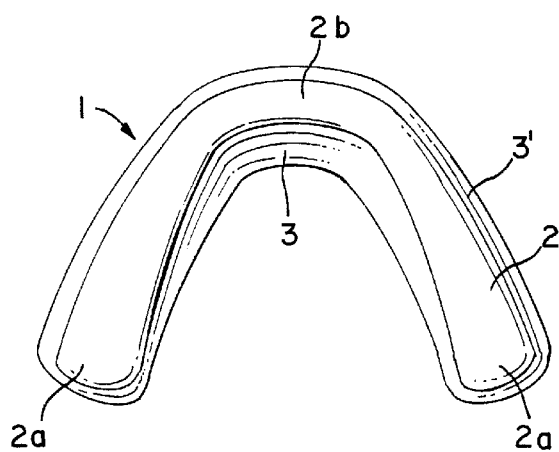
FIG. 5
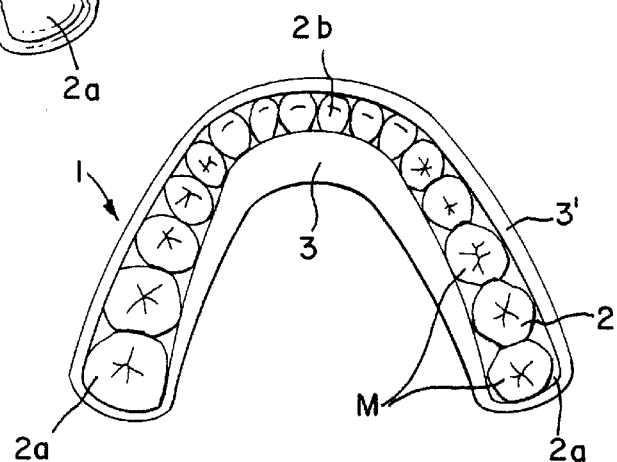
FIG. 6
FIG. 7
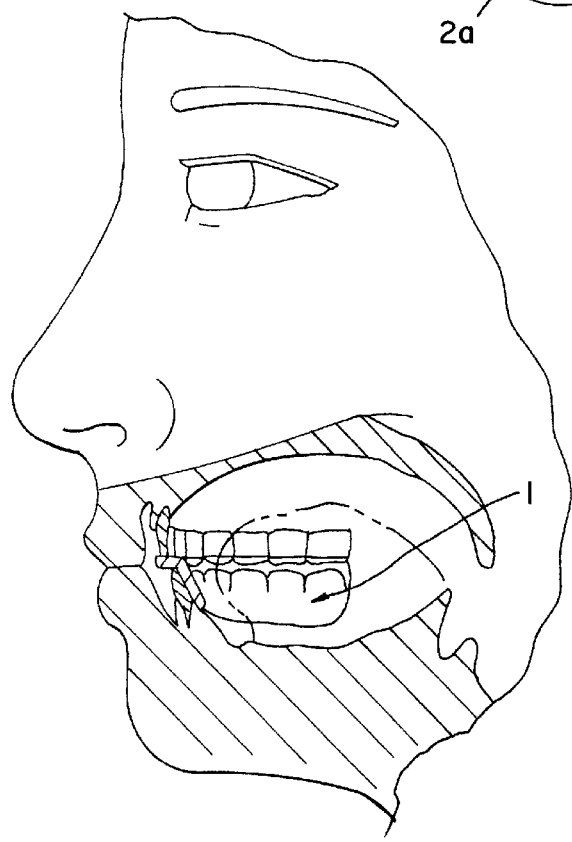
FIG. 8
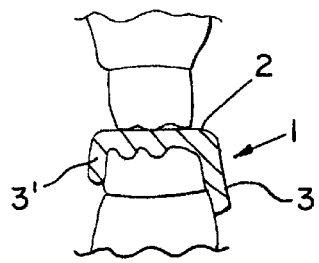

DENTAL PROTECTOR AGAINST BRUXISM

This application is a 371 of Pct/JP99/00145, filed Jan. 18, 1999.

TECHNICAL FIELD

This invention relates to a dental protector for prevention of the nuisance associated with bruxism, i.e. clenching of the teeth, which is mounted on the teeth at bedtime.

BACKGROUND ART

While some persons grind their teeth unconsciously during sleep, this phenomenon known as bruxism produces noises offensive to the ear, causing a great nuisance to their roommates in many cases. Moreover, as bruxism becomes severe, it imposes so great a burden on one's own teeth that the teeth are sometimes worn or injured.

Therefore, it is common practice that the dentist takes an impression of the oral cavity to fabricate a plaster cast and causes a filled acrylic resin material to polymerize in suit to construct a dental protector conforming to the upper and lower teeth, and let the patient wear the device.

However, as far as the conventional dental protector against bruxism is concerned, the dentist has to go through a tedious procedure comparable to the work required for construction of a denture but the procedure involves many time-consuming steps, some of which require a high degree of skill, with the result that the cost of production is inevitably high.

Having been developed in view of the above state of the art, this invention has for its object to provide a dental protector against bruxism which is effective in preventing generation of the offensive noise due to clenching of the teeth during sleep and reducing the burden on the teeth for protecting the teeth and, in addition, is improved in the stability or securedness as mounted on the teeth, easy to fabricate, and fitting to many persons in common.

DISCLOSURE OF THE INVENTION

Developed to accomplish the above object, the dental protector against bruxism according to this invention comprises a protective part configured generally in the form of the letter U in conformity with the dental arc and adapted to cover the occlusal faces of the teeth and an engaging part contiguous to the inner circumference of said protective part and adapted to cover the posterior surfaces of the teeth, a lower stratum of said protective part which is to contact the teeth and said engaging part contiguous thereto being formed from a thermoplastic resin having a softening temperature lower than the boiling temperature of water while the upper stratum of said protective part which has a flat surface being formed from a material which does not soften at said softening temperature.

BRIEF DESCRIPTION OF THE DRAWINGS

FIG. 1 is a perspective view showing a dental protector against bruxism according to one embodiment of the invention.

FIG. 2(A) is an end view taken along the line A—A of FIG. 1 and FIG. 2(B) is an end view taken along the line B—B of FIG. 1.

FIG. 3 is a front view of the dental protector against bruxism shown in FIG. 1.

FIG. 4 is a left side view of the dental protector against bruxism shown in FIG. 1.

FIG. 5 is a back view of the dental protector against bruxism shown in FIG. 1.

FIG. 6 is a back view of the dental protector of FIG. 1 which has been given an impression mark of the teeth.

FIG. 7 is a view showing the dental protector of FIG. 1 in use.

FIG. 8 is a cross-section view showing the mode of engagement of the dental protector with the molar tooth in use of the protector.

BEST MODE FOR CARRYING OUT THE INVENTION

The dental protector against bruxism according to one embodiment of this invention is now described, reference being had to the accompanying drawings.

FIG. 1 is a perspective view showing a specific dental protector against bruxism according to this invention, FIG. 2(A) is an end view taken along the line A—A of FIG. 1 and FIG. 2(B) is an end view taken along the line B—B. FIG. 3 through FIG. 5 are a front view, a left side view and a back view, respectively, of said protector against bruxism.

The dental protector against bruxism according to this invention is used as mounted on either the upper teeth (dentes superior) or the lower teeth (dentes inferior), and maybe used as attached to the upper teeth. In terms of stability, however, it is preferably mounted on the lower teeth. Therefore, this embodiment will be described below in detail with reference to the use of the protector on the lower teeth.

The dental protector against bruxism 1 is configured generally in the form of the letter U in conformity with the dental arc and comprises a protective part 2 adapted to cover the occlusal faces of the teeth and an engaging part 3 contiguous to the inner circumference of said protective part 2 and adapted to cover the posterior surfaces of the teeth. In longitudinal section, the dental protector 1 is generally L-configured.

The protective part 2 mentioned above is a binary layer structure consisting of a lower stratum 2y which is to rest directly on the teeth and a planar upper stratum 2x which is to be abutted against the occlusal faces of the upper teeth, with said contiguous engaging part 3 projecting downwards from the inner circumferential edge of said lower stratum 2y.

The lower stratum 2y of the protective part 2 and the engaging part 3 are formed from a thermoplastic resin. As the thermoplastic resin, a resin material having a softening temperature (e.g. 50–90° C.) higher than the human body temperature but lower than the boiling temperature of water is used. More particularly, an ethylene-vinyl acetate copolymer is used with advantage, although polyurethane, silicone resin, poly(vinyl acetate), etc. may also be used likewise.

On the other hand, the upper stratum 2x of the protective part 2 is formed with a flat surface from a material which does not soften at said softening temperature. The preferred material for this upper stratum 2x includes elastomers, with silicone rubber or silicone elastomer being particularly preferred.

It should be understood that both the upper stratum 2x and lower stratum 2y may optionally be formed from, for example, ethylene-vinyl acetate copolymer.

The radial dimension W of the protective part 2 is greatest in the molar region 2a at the termini of the dental protector against bruxism 1 and diminishes gradually towards the incisor or front tooth region 2b.

The curvature of the protective part 2 can be advantageously selected with reference to the stockpile of dental arc data generated in denture making and when a given curved shape is thus selected, the dental protector against bruxism 1 molded using a single plaster cast may be applicable to many persons, thus contributing to cost reduction.

The engaging part 3 is contiguous to the inner circumference of the protective part 2 and adapted to cover the posterior surfaces of the teeth. Thus, in order that it may snugly abut against the posterior surfaces of the teeth from the inner edges of the occlusal faces, the engaging part 3 projects out downwards from the lower stratum 2y of the protective part 2. As a result, the longitudinal cross-section of the dental protector against bruxism 1 is generally L-configured.

Optionally, the outer circumference of the protective part 2 may also be provided with an engaging part 3' projecting a small distance downwards. In this case, the height of the engaging part 3' along said outer circumference may be smaller than the length L of the engaging part 3 on the inner circumference of the protective part 2. As the outer circumference of the protective part 2 is thus provided with the engaging part 3', the dental protector against bruxism 1 can be positioned more accurately and locked more securely in position.

The engaging part 3 has a length L of 2~13 mm as measured from the top surface of the upper stratum 2x of the protective part 2 and, in order that it may fit the posterior side of the row of teeth more snugly and insure improved stability after mounting on the teeth, is preferably formed comparatively longer in the molar tooth region 2a and somewhat shorter in the front tooth region 2b.

As illustrated in FIG. 4, the engaging part 3 is recessed by 5~10 mm at the termini of its molar regions. This recess is provided to minimize the foreign body sensation during wear and does not interfere with the function of the dental protector against bruxism.

The thickness S of the upper and lower strata, combined, of the protective part 2 is generally 1~4 mm in the molar region 2a and 3~8 mm in the front tooth region. In the illustrated embodiment, the thickness S is 2 mm in the molar region, 4 mm in the front tooth region, and about 3 mm in the intermediate region, and the thickness of the front tooth region is about 2~5 times as great as the thickness of the molar tooth regions. These dimensional proportions are chosen in consideration of the usual condition that the ratio of the biting thickness of the molar and that of the front tooth is about 1:3~5.

The thickness of the lower stratum 2y of the protective part 2 and the thickness of the engaging part 3 contiguous to its inner circumference should be large enough to allow an ethylene-vinyl acetate copolymer or the like material to be given an impression mark of teeth by the method described hereinafter so that the dental protector 1 will not be dislodged during sleep. In this embodiment, for instance, the thickness t is 1~4 mm.

The dental protector against bruxism 1 according to this embodiment may be formed to have a straight profile but, as shown in FIG. 4, preferably have a profile slightly curved in the direction of the protective part 2 towards the molars.

The use of the dental protector against bruxism 1 of this embodiment is now described.

Prior to use, the dental protector 1 is given an impression mark M engageable with one's teeth in accordance with the following procedure.

(1) First, according to its raw material, the dental protector against bruxism 1 is immersed in hot water, for example at about 50~90° C., for about 10 seconds ~1 minute to warm it to said softening temperature, whereby the lower stratum 2y of the protective part 2 and the engaging part 3 are rendered soft and flexible. In this connection, both ends of the dental protector 1 may be cut off with a pair of scissors or the like beforehand so that the protector may be better fitted to the user.

(2) Then, the warmed dental protector 1 is inserted into the oral cavity and its engaging part 3 is positioned in intimate contact with the posterior surfaces of the teeth. In this condition, the user clenches the upper and lower teeth against each other to make an impression mark M conforming to the shape of his or her teeth in said lower stratum 2y and engaging part 3 (3') which have been softened as above.

(3) The dental protector against bruxism 1 given the impression mark M of teeth in the above manner is cooled to a temperature below said softening temperature over about 10 seconds ~1 minute to thereby harden the protector 1. In this manner, a finished detail protector provided with said impression mark M conforming to the user's teeth in the lower stratum 2y of protective part 2 and the engaging part 3 (3') as illustrated in FIG. 6 is obtained.

For use of this dental protector against bruxism 1, the protector 1 formed with said impression mark M is inserted into the oral cavity at bedtime and mounted on the teeth by bringing the impression mark M formed in the lower stratum 2y of the protective part 2 into engagement with the teeth as shown in FIG. 7.

When the dental protector against bruxism 1 is mounted on the lower teeth, the lower teeth are intimately engaged by the impression mark M formed in both the lower stratum 2y of protective part 2 and the engaging part 3 (3') as shown in FIG. 8 so that it does not happen that the dental protector is disengaged from the teeth during sleep. FIG. 8 shows the status of engagement of the dental protector 1 with the molars.

As the dental protector against bruxism 1 is mounted on the lower teeth, clenching of one's teeth does not bring the upper and lower teeth into direct mutual contact, with the result that not only the generation of offensive noises is prevented but the burden on the teeth is alleviated so that the wear and breakage of the teeth can be precluded. Moreover, the top surface of the upper stratum 2y of the protective part 2, which is abutted against the upper teeth, is flat and smooth, without being provided with said impression mark of the teeth, the above-mentioned effects are more positively insured.

Industrial Applicability

The dental protector against bruxism according to this invention can be expediently used by immersing it in hot water and molding it in conformity with one's teeth. Therefore, a dental protector against bruxism can be easily obtained whether at home or in a hotel or the like to positively prevent clenching of one's teeth.

What is claimed is:

1. A dental protector against bruxism comprising: a protective part generally in the form of a dental arch and adapted to engage contiguous occlusal faces of a row of teeth; and an engaging part contiguous with an inner circumference of said protective part and adapted to engage continuous posterior surfaces of a row of teeth, a lower stratum of said protective part adapted to contact the row of teeth and said engaging part contiguous thereto formed from a thermoplastic resin having a softening temperature lower than the boiling temperature of water, and an upper stratum of said protective part having a flat surface formed from a material which does not soften at said softening temperature.

2. The dental protector against bruxism according to claim 1 wherein said upper stratum of said protective part, said lower stratum of said protective part, and said engaging part are formed from the same material.

3. The dental protector against bruxism according to claim 2, wherein said thermoplastic resin has a softening temperature within the range of 50–90° C.

4. The dental protector against bruxism according to claim 2, wherein said protective part measures 1–4 mm in thickness in molar regions and 3–8 mm in a front tooth region and has an occlusal face which is narrower in said front teeth region than in said molar tooth regions.

5. The dental protector against bruxism according to claim 2, wherein said engaging part is 1–4 mm in thickness and 2–13 mm in height as measured from a top surface of said upper stratum of said protective part.

6. The dental protector against bruxism according to claim 1 wherein said thermoplastic resin has a softening temperature within the range of 50–90° C.

7. The dental protector against bruxism according to claim 6, wherein said protective part measures 1–4 mm in thickness in molar regions and 3–8 mm in a front tooth region and has an occlusal face which is narrower in said front teeth region than in said molar tooth regions.

8. The dental protector against bruxism according to claim 6, wherein said engaging part is 1–4 mm in thickness and 2–13 mm in height as measured from a top surface of said upper stratum of said protective part.

9. The dental protector against bruxism according to claim 1 wherein said protective part measures 1–4 mm in thickness in a pair of molar regions and 3–8 mm in a front tooth region and has an occlusal face which is narrower in said front tooth region than in said molar tooth regions.

10. The dental protector against bruxism according to claim 9, wherein said engaging part is 1–4 mm in thickness and 2–13 mm in height as measured from a top surface of said upper stratum of said protective part.

11. The dental protector against bruxism according to claim 1 wherein said engaging part is 1–4 mm in thickness and 2–13 mm in height as measured from a top surface of said upper stratum of said protective part.

\* \* \* \* \*